US008821524B2

(12) United States Patent
Agahi

(10) Patent No.: US 8,821,524 B2
(45) Date of Patent: Sep. 2, 2014

(54) FEEDBACK CONTROL OF ON/OFF PNEUMATIC ACTUATORS

(75) Inventor: Daryush Agahi, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1 day.

(21) Appl. No.: 12/788,609

(22) Filed: May 27, 2010

(65) Prior Publication Data

US 2011/0295293 A1 Dec. 1, 2011

(51) Int. Cl.
*A61B 17/32* (2006.01)
*A61B 19/02* (2006.01)
*A61F 9/007* (2006.01)
*A61B 17/00* (2006.01)

(52) U.S. Cl.
CPC ... *A61B 19/0248* (2013.01); *A61B 2017/00544* (2013.01); *A61B 2017/00154* (2013.01); *A61B 2019/025* (2013.01); *A61F 9/00763* (2013.01)
USPC .......................................... 606/167; 606/170

(58) Field of Classification Search
CPC ............... A61B 17/320068; A61B 17/320758; A61B 17/320783; A61B 17/32075; A61F 9/00736; A61F 9/00754
USPC ......... 606/159, 160, 170, 171, 175, 176, 178, 606/179, 180; 137/557, 624.12, 624.18
See application file for complete search history.

(56) References Cited

U.S. PATENT DOCUMENTS

| 812,162 A | 2/1906 | Bemis |
| 2,016,746 A | 10/1935 | Ireland |
| 2,707,389 A | 5/1955 | Fortier |
| 3,084,674 A | 4/1963 | Watson |
| 3,477,665 A | 11/1969 | Legrand |
| 3,646,727 A | 3/1972 | Wachsmuth |
| 3,703,139 A | 11/1972 | Furlong |
| 3,815,604 A | 6/1974 | O'Malley et al. |
| 3,854,382 A | 12/1974 | Walters et al. |
| 3,867,934 A | 2/1975 | Ollivier |

(Continued)

FOREIGN PATENT DOCUMENTS

| DE | 3708989 | 10/1988 |
| DE | 3925405 A1 | 2/1991 |

(Continued)

OTHER PUBLICATIONS

Kabei, N. et al., "A portable pneumatic driving unit for a left ventricular assist device", Int. J. Artif. Organs, 1988, pp. 186-190, vol. 11:3.
Nachlas, M. N. et al., "A Simple Portable Pneumatic Pump for External Cardiac Massage", Am. J. of Cardiol., Jul. 1962, pp. 107-109, vol. 10:1.

(Continued)

*Primary Examiner* — Tuan V Nguyen

(57) ABSTRACT

A surgical system having feedback control for pneumatic actuators includes a pneumatic pressure source and a vitrectomy cutter having a cutting mechanism, a first pneumatic input port, and a second pneumatic input port. A pneumatic actuator is configured to direct pneumatic pressure to one of the first and second pneumatic input ports. A first pressure transducer is located and configured to detect actual pressure at the first pneumatic input port, and a second pressure transducer is located and configured to detect actual pressure at the second pneumatic input port. A controller communicates with the first and second pressure transducers and the pneumatic actuator. It is configured to change the pneumatic actuator actuation timing based on the data communicated from the first and second pressure transducers.

19 Claims, 4 Drawing Sheets

(56) References Cited

U.S. PATENT DOCUMENTS

| | | |
|---|---|---|
| 4,011,869 A | 3/1977 | Seiler, Jr. |
| 4,077,567 A | 3/1978 | Ginn et al. |
| 4,086,804 A | 5/1978 | Ruby |
| 4,164,167 A | 8/1979 | Imai et al. |
| 4,168,707 A | 9/1979 | Douvas et al. |
| 4,253,480 A | 3/1981 | Kessel et al. |
| 4,255,789 A | 3/1981 | Hartford |
| 4,323,064 A | 4/1982 | Hoenig et al. |
| 4,331,130 A | 5/1982 | Lewicky |
| 4,335,867 A | 6/1982 | Bihlmaier |
| 4,344,144 A | 8/1982 | Damico et al. |
| 4,368,734 A | 1/1983 | Banko |
| 4,476,532 A | 10/1984 | Akiyama et al. |
| 4,590,935 A | 5/1986 | Ranalli |
| 4,622,503 A | 11/1986 | Sundblom et al. |
| 4,650,460 A | 3/1987 | Roizenblatt |
| 4,650,462 A | 3/1987 | DeSatnick et al. |
| 4,678,459 A | 7/1987 | Onik et al. |
| 4,679,583 A | 7/1987 | Lucas et al. |
| 4,696,298 A | 9/1987 | Higgins et al. |
| 4,706,687 A | 11/1987 | Rogers |
| 4,757,814 A | 7/1988 | Wang et al. |
| 4,770,654 A | 9/1988 | Rogers et al. |
| 4,790,816 A | 12/1988 | Sundblom et al. |
| 4,810,242 A | 3/1989 | Sundblom et al. |
| 4,840,111 A | 6/1989 | Garnjost |
| 4,933,843 A | 6/1990 | Scheller et al. |
| 4,985,027 A | 1/1991 | Dressel |
| 5,019,035 A | 5/1991 | Missirlian et al. |
| 5,020,315 A | 6/1991 | Leachman, Jr. et al. |
| 5,020,825 A | 6/1991 | Lizell |
| 5,024,654 A | 6/1991 | Tyler |
| 5,047,008 A | 9/1991 | de Juan, Jr. et al. |
| 5,092,178 A | 3/1992 | Vanderlann |
| 5,094,260 A | 3/1992 | Stuart et al. |
| 5,106,364 A | 4/1992 | Hayafuji et al. |
| 5,138,564 A | 8/1992 | de Jong et al. |
| 5,154,207 A | 10/1992 | Bolt |
| 5,176,628 A | 1/1993 | Charles et al. |
| 5,217,465 A | 6/1993 | Steppe |
| 5,239,861 A | 8/1993 | Fujita et al. |
| 5,314,295 A | 5/1994 | Lukkari et al. |
| 5,380,280 A | 1/1995 | Peterson |
| 5,403,276 A | 4/1995 | Schechter et al. |
| 5,417,246 A | 5/1995 | Perkins et al. |
| 5,437,241 A | 8/1995 | Rosenberg et al. |
| 5,445,773 A | 8/1995 | Arai |
| 5,457,625 A | 10/1995 | Lim et al. |
| 5,549,139 A | 8/1996 | Perkins et al. |
| 5,550,685 A | 8/1996 | Drouin |
| 5,571,248 A | 11/1996 | Seetharaman et al. |
| 5,580,347 A | 12/1996 | Reimels |
| 5,587,536 A | 12/1996 | Rasmussen |
| 5,630,827 A | 5/1997 | Vijfvinkel |
| 5,674,194 A | 10/1997 | Jung et al. |
| 5,791,142 A | 8/1998 | Layne et al. |
| 5,808,396 A | 9/1998 | Boukhny |
| 5,810,765 A | 9/1998 | Oda |
| 5,829,335 A | 11/1998 | Ewald et al. |
| 5,846,257 A | 12/1998 | Hood |
| 5,857,485 A | 1/1999 | Perkins et al. |
| 5,959,390 A | 9/1999 | Boukhny |
| 5,979,494 A | 11/1999 | Perkins et al. |
| 5,989,262 A | 11/1999 | Josephberg |
| 5,993,409 A | 11/1999 | Maaskamp |
| 6,155,233 A | 12/2000 | Wade et al. |
| 6,162,187 A | 12/2000 | Buzzard et al. |
| 6,425,883 B1 | 7/2002 | Urich et al. |
| 6,450,966 B1 | 9/2002 | Hanna |
| 6,485,436 B1 | 11/2002 | Truckai et al. |
| 6,514,268 B2 * | 2/2003 | Finlay et al. .................. 606/170 |
| 6,575,264 B2 | 6/2003 | Spadafora |
| 6,575,990 B1 | 6/2003 | Wang et al. |
| 6,678,584 B2 | 1/2004 | Junk et al. |
| 6,730,106 B2 | 5/2004 | Kanda et al. |
| 6,773,445 B2 * | 8/2004 | Finlay et al. .................. 606/170 |
| 6,779,541 B2 | 8/2004 | Inayama et al. |
| 6,848,323 B2 | 2/2005 | Krouth et al. |
| 6,851,453 B2 * | 2/2005 | Lipscomb et al. ............ 138/104 |
| 6,892,745 B2 | 5/2005 | Benson |
| 6,954,683 B2 | 10/2005 | Junk et al. |
| 6,999,853 B2 | 2/2006 | Junk et al. |
| 7,244,240 B2 | 7/2007 | Nazarifar et al. |
| 7,254,452 B2 | 8/2007 | Davlin |
| 7,263,877 B2 | 9/2007 | Schaefer et al. |
| 7,283,321 B1 | 10/2007 | Sun et al. |
| 7,335,217 B2 | 2/2008 | Wang et al. |
| 7,337,041 B2 | 2/2008 | Junk et al. |
| 7,352,287 B2 | 4/2008 | Rupert |
| 7,470,277 B2 | 12/2008 | Finlay et al. |
| 7,600,405 B2 | 10/2009 | Maurer, Jr. et al. |
| 7,628,054 B2 | 12/2009 | Hajishah et al. |
| 7,640,119 B2 | 12/2009 | Khashayar |
| 7,708,734 B2 | 5/2010 | Khashayar |
| 7,775,052 B2 | 8/2010 | Cornwell et al. |
| 8,038,692 B2 | 10/2011 | Valencia et al. |
| 8,157,145 B2 | 4/2012 | Shelton, IV et al. |
| 8,187,293 B2 | 5/2012 | Kirchhevel |
| 8,202,277 B2 | 6/2012 | Ryan |
| 8,215,108 B2 | 7/2012 | Hahn et al. |
| 8,230,877 B2 | 7/2012 | Roberge et al. |
| 8,308,737 B2 | 11/2012 | Ryan |
| 8,312,800 B2 | 11/2012 | Turner et al. |
| 2002/0117214 A1 | 8/2002 | Tucker et al. |
| 2003/0042182 A1 | 3/2003 | Moscaritolo |
| 2003/0195538 A1 | 10/2003 | Wang et al. |
| 2003/0208305 A1 | 11/2003 | Junk et al. |
| 2004/0154466 A1 | 8/2004 | Gethmann et al. |
| 2004/0186484 A1 | 9/2004 | Ryan |
| 2005/0033309 A1 | 2/2005 | Ryan |
| 2005/0245909 A1 | 11/2005 | McCary et al. |
| 2006/0129062 A1 | 6/2006 | Nicoson et al. |
| 2006/0271082 A1 | 11/2006 | Kirchhevel et al. |
| 2007/0093793 A1 | 4/2007 | Maurer, Jr. et al. |
| 2007/0185512 A1 | 8/2007 | Kirchhevel |
| 2007/0219647 A1 | 9/2007 | Heertjes et al. |
| 2007/0270735 A1 | 11/2007 | Williams et al. |
| 2007/0270746 A1 | 11/2007 | King |
| 2007/0282262 A1 | 12/2007 | Williams et al. |
| 2008/0082077 A1 | 4/2008 | Williams |
| 2008/0103433 A1 * | 5/2008 | Nazarifar et al. ................ 604/31 |
| 2008/0108980 A1 | 5/2008 | Turner et al. |
| 2008/0110236 A1 * | 5/2008 | Hajishah et al. ................ 73/1.64 |
| 2008/0142093 A1 | 6/2008 | Turner et al. |
| 2008/0146988 A1 | 6/2008 | Olivera et al. |
| 2008/0149197 A1 | 6/2008 | Turner et al. |
| 2008/0154292 A1 | 6/2008 | Huculak |
| 2008/0168985 A1 | 7/2008 | Turner et al. |
| 2008/0172077 A1 | 7/2008 | Valencia et al. |
| 2008/0300580 A1 | 12/2008 | Shelton, IV et al. |
| 2009/0082715 A1 | 3/2009 | Charles et al. |
| 2009/0124962 A1 | 5/2009 | Hopkins et al. |
| 2009/0203480 A1 | 8/2009 | Petzold et al. |
| 2009/0259242 A1 | 10/2009 | Gerg et al. |
| 2009/0287233 A1 | 11/2009 | Huculak |
| 2009/0305214 A1 | 12/2009 | Pybus et al. |
| 2010/0145374 A1 | 6/2010 | Perkins et al. |
| 2010/0305596 A1 | 12/2010 | Peterson et al. |
| 2010/0312169 A1 | 12/2010 | Auld et al. |
| 2011/0005387 A1 | 1/2011 | Ehre et al. |
| 2011/0054508 A1 * | 3/2011 | Zhou et al. .................... 606/170 |
| 2011/0144675 A1 | 6/2011 | Gao et al. |
| 2011/0295293 A1 | 12/2011 | Agahi |
| 2011/0299943 A1 | 12/2011 | Woolever |
| 2012/0010602 A1 | 1/2012 | Ryan |
| 2012/0055329 A1 | 3/2012 | Heer |
| 2012/0157906 A1 | 6/2012 | Underwood |
| 2012/0157907 A1 | 6/2012 | Underwood |
| 2012/0157908 A1 | 6/2012 | Underwood |
| 2012/0157909 A1 | 6/2012 | Underwood |
| 2012/0158006 A1 | 6/2012 | McDonell |

(56) References Cited

U.S. PATENT DOCUMENTS

| | | |
|---|---|---|
| 2012/0158029 A1 | 6/2012 | Underwood |
| 2012/0158030 A1 | 6/2012 | Underwood |
| 2012/0221033 A1 | 8/2012 | Auld et al. |

FOREIGN PATENT DOCUMENTS

| | | |
|---|---|---|
| DE | 4232586 A1 | 3/1994 |
| DE | 19821420 C1 | 10/1999 |
| DE | 10247869 A1 | 5/2004 |
| DE | 202005009670 U1 | 9/2005 |
| DE | 10247869 A1 | 2/2007 |
| DE | 102006030034 | 1/2008 |
| EP | 0469641 B1 | 1/1987 |
| EP | 0626628 A1 | 11/1994 |
| EP | 0626628 B1 | 11/1994 |
| EP | 0673475 B1 | 6/1996 |
| EP | 0874163 A2 | 10/1998 |
| EP | 874163 A2 | 10/1998 |
| EP | 0884667 A1 | 12/1998 |
| EP | 0874163 A3 | 3/1999 |
| EP | 1074271 A2 | 2/2001 |
| EP | 1074271 A3 | 2/2002 |
| EP | 1172586 B1 | 3/2004 |
| EP | 1074271 B1 | 10/2004 |
| EP | 1660244 B1 | 12/2006 |
| EP | 2032878 B1 | 12/2009 |
| GB | 792397 A | 3/1958 |
| GB | 1189493 A | 6/1970 |
| GB | 1213723 | 11/1970 |
| GB | 1 323 788 A | 7/1973 |
| GB | 1417299 A | 12/1975 |
| GB | 2016746 A | 9/1979 |
| GB | 2 140 871 A | 12/1984 |
| GB | 2203195 A | 10/1988 |
| GB | 2389423 A | 12/2003 |
| JP | 07259801 A | 10/1995 |
| JP | 09225698 A | 9/1997 |
| JP | 9311091 A | 12/1997 |
| JP | 2010057642 A | 3/2010 |
| WO | 92/02866 A1 | 2/1992 |
| WO | 93/18445 A1 | 9/1993 |
| WO | 9531141 A1 | 11/1995 |
| WO | 98/25556 A1 | 6/1998 |
| WO | 9825556 A1 | 6/1998 |
| WO | 0078371 A1 | 12/2000 |
| WO | WO 0130281 A1 | 5/2001 |
| WO | 0164120 A1 | 9/2001 |
| WO | 2008000599 A1 | 1/2008 |
| WO | 20081029066 A1 | 3/2008 |
| WO | 2008054944 A1 | 5/2008 |
| WO | WO 2008079526 A2 | 7/2008 |
| WO | WO 2008079526 A3 | 8/2008 |
| WO | 2008105950 A2 | 9/2008 |
| WO | 2008140537 A1 | 11/2008 |
| WO | 2008147429 A2 | 12/2008 |
| WO | WO 2008147429 A3 | 3/2009 |
| WO | WO 2008105950 A3 | 9/2009 |
| WO | WO 2010/066302 A1 | 6/2010 |
| WO | WO 2011/025658 A1 | 3/2011 |
| WO | 2011071613 A1 | 6/2011 |
| WO | WO 2011/071655 A1 | 6/2011 |
| WO | 2011138102 A1 | 11/2011 |
| WO | WO 2011/149621 A1 | 12/2011 |

OTHER PUBLICATIONS

Waldeck, J. L., "The Development of a Portable Pressure Source for the Static and Dynamic Calibration of Pressure Transducers", J. Wind Eng. Ind. Aerodynamics, 1987, pp. 213-230, vol. 26:2.

Ellis, B. P. et al., "Microcomputer-Controlled Precision Pneumatic Pressure Generator", IEEE Trans. on Instrum. Meas., Sep. 1977, pp. 214-217, vol. 26:3.

Whalen, R. L. et al., "An Electromagnetic Pneumatic Blood Pump Driver." Am. Soc. of Artificial Internal Organs, 1988, pp. 721-725, vol. 34:3.

Turkentine, R. B. et al., "Pressure-operated shutter for thin-film monitor", J. Phys. E: Sci. Instrum., 1979, p. 17, vol. 12:1.

Rogers, R. C., "An Inexpensive Picoliter-Volume Pressure Ejection System", Brain Res. Bulletin, May 1985, pp. 669-671, vol. 15:6.

Johnson, K. S. et al., "A Submersible Flow Analysis System", Analytica Chimica Acta, Sep. 1986, pp. 245-257, vol. 179.

Tabassum, A. A., "Solar refrigeration: evaluation of technical options and design of a solar-generator-adsorber for a novel adsorption refrigerator", PhD and Masters by Research Theses, Cranfield University, School of Engineering, 1989; Abstract only. LINK: http://hdl.handle.net/1826/4213.

Buchanan, P. R. et al., "Recovery of ventilation distributions by gas wash-out of a mechanical pump", Clin. Phys. Physiol. Meas., 1986, pp. 237-252, vol. 7:3.

Gao, Shawn, et al., "Systems and Methods for Dynamic Pneumatic Valve Driver," U.S. Appl. No. 12/944,039, filed Nov. 11, 2010, 31 pgs.

Zhou, Jason, et al., "Pneumatic Pressure Output Control by Drive Valve Duty Cycle Calibration," U.S. Appl. No. 12/854,281, filed Aug. 11, 2010, 38 pgs.

International Searching Authority, International Search Report, PCT/US2010/056305, Mar. 2, 2011, 3 pages.

International Searching Authority, Written Opinion of the International Searching Authority, PCT/US2010/056305, Mar. 2, 2011, 7 pages.

International Searching Authority, International Search Report, PCT/US2010/045136, Nov. 18, 2010, 4 pages.

International Searching Authority, Written Opinion of the International Searching Authority, PCT/US2010/045136, Nov. 18, 2010, 6 pages.

International Searching Authority, International Search Report, PCT/US2011/034720, Jul. 28, 2011, 2 pages.

International Searching Authority, Written Opinion of the International Searching Authority, PCT/US2011/034720, Jul. 20, 2011, 8 pages.

Nguyen, Tuan Van, Non-Final Office Action, U.S. Appl. No. 12/944,039, Mar. 5, 2013, 29 pgs.

International Searching Authority, International Search Report, PCT/US2012/049695, Oct. 24, 2012, 2 pages.

International Searching Authority, Written Opinion of the International Searching Authority, PCT/2012/049695, Oct. 24, 2012, 4 pages.

European Patent Office, Supplementary European Search Report, Application No. 11787078.2, Publication No. 2575633, Published Apr. 10, 2013, 8 pages.

* cited by examiner

FEEDBACK CONTROL OF ON/OFF PNEUMATIC ACTUATORS

BACKGROUND OF THE INVENTION

The present invention pertains to pneumatic actuators. More particularly, but not by way of limitation, the present invention pertains to feedback control of on/off pneumatic actuators usable with a vitrectomy probe.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g. cutting and removal of vitreous near a detached portion of the retina or a retinal tear), vitreous base dissection, and cutting and removal of membranes are particularly difficult.

The use of microsurgical cutting probes in posterior segment ophthalmic surgery is well known. These cutting probes typically include a hollow outer cutting member, a hollow inner cutting member arranged coaxially with and movably disposed within the hollow outer cutting member, and a port extending radially through the outer cutting member near the distal end thereof. Vitreous humor and/or membranes are aspirated into the open port, and the inner member is actuated, closing the port. Upon the closing of the port, cutting surfaces on both the inner and outer cutting members cooperate to cut the vitreous and/or membranes, and the cut tissue is then aspirated away through the inner cutting member.

During surgical procedures, cutting rates and duty cycle are frequently controlled to regulate the amount of tissue that can be cut in a given time period. For example, when cutting in less sensitive areas, such as areas spaced from the retina, the cutting may be done in a manner that lends to efficiency. When cutting in more sensitive areas, such as those nearer to the retina, the cutting may be done in a careful manner, where the amount of tissue cut per cutting cycle is decreased. This is accomplished by controlling the duty cycle, or the percentage of time in a cutting cycle that a port is open. This is determined by dividing the amount of time the port is open by the total amount of time of a single cutting cycle. Larger duty cycles provide for efficient cutting while smaller duty cycles provide for slow and careful cutting.

Variations in characteristics of cutter components, including those from initial critical component tolerances, can introduce inconsistencies in duty cycles across cutters. To address this, current systems are calibrated at the time of manufacturing. This factory calibration can be a time consuming and costly activity. Further, it is done with the assumption that changes over time of these same critical components will not significantly affect performance. This assumption however, may not be valid in many cases. As components become worn over time, the precision and accuracy of controlled parameters may become adversely affected. These variations can potentially degrade the performance of the system or even prevent the system from reaching its desired operating targets, potentially resulting in a cutter that does not fully open or close. These performance degradations and failures become more pronounced and more frequent through continued use.

Despite the above described advances, a need still exists for improved vitrectomy probes. In particular, vitrectomy probes that compensate for discrepancies arising from initial tolerances or degradations of components over time.

The present disclosure is directed to addressing one or more of the deficiencies in the prior art.

SUMMARY OF THE INVENTION

In one exemplary aspect consistent with the principles herein, the present disclosure is directed to a surgical system having feedback control for pneumatic actuators. The system includes a pneumatic pressure source and a vitrectomy cutter having a cutting mechanism, a first pneumatic input port, and a second pneumatic input port. A pneumatic actuator is configured to direct pneumatic pressure to one of the first and second pneumatic input ports. A first pressure transducer is located and configured to detect actual pressure at the first pneumatic input port, and a second pressure transducer is located and configured to detect actual pressure at the second pneumatic input port. A controller communicates with the first and second pressure transducers and the pneumatic actuator. It is configured to change the pneumatic actuator actuation timing based on the data communicated from the first and second pressure transducers.

In another exemplary aspect, the present disclosure is directed to a method of controlling a surgical system using feedback control for pneumatic actuators. The method includes steps of selectively directing pneumatic pressure to one of first and second pneumatic input ports on a vitrectomy cutter, detecting actual pressure at the first pneumatic input port with a first pressure transducer, and detecting actual pressure at the second pneumatic input port with a second pressure transducer. The method also includes modifying actuation timing of the pneumatic actuator based on the actual pressures detected by the first and second pressure transducers.

In another exemplary aspect, the present disclosure is directed to a surgical system having feedback control for pneumatic actuators. It includes a pneumatic pressure source and a vitrectomy cutter having a cutting mechanism, a first pneumatic input port, and a second pneumatic input port. A pneumatic actuator directs pneumatic pressure to one of the first and second pneumatic input ports. A first pressure transducer is placed and configured to detect pressure at the first pneumatic input port, and a second pressure transducer placed and configured to detect pressure at the second pneumatic input port. A controller communicates with the first and second pressure transducers and the pneumatic actuator. The controller is configured to compare the parameter data based on actual measured data to stored desired data and calculate a margin based on the parameter data and the stored data. It also is configured to modify a stored operating parameter for a particular duty cycle and generate control signals based on the modified operating parameter for communication to the pneumatic actuator. In one exemplary aspect, the pneumatic actuator is a first pneumatic actuator and a second pneumatic actuator, the first pneumatic actuator being configured to direct pneumatic pressure to the first second pneumatic port and the second pneumatic actuator being configured to direct pneumatic pressure to the second pneumatic port.

It is to be understood that both the foregoing general description and the following detailed description are exemplary and explanatory only and are intended to provide further explanation of the invention as claimed. The following description, as well as the practice of the invention, sets forth and suggests additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to exemplary embodiments of the invention, examples of which are illustrated in the accompanying drawings. Wherever possible, the same reference numbers are used throughout the drawings to refer to the same or like parts.

The present disclosure is directed to a surgical system including a vitrectomy cutter for performing ophthalmic surgeries. The surgical system is arranged and configured to use feedback control to detect and to compensate for deviations in operation due to inconsistencies arising from individual component tolerances or degradation. Particularly, the feedback control can reduce the overall sensitivity of the system to individual component tolerances, variations, and overall deviations from desired characteristics. This approach can potentially accommodate a wider range of critical component tolerances, and can compensate for changes or variations resulting from component ageing or adverse environmental effects, such as temperature. Using the feedback control, the system is arranged and configured to identify when operating parameters are outside of acceptable ranges and to use control laws to modify the operating parameters to place them back within acceptable ranges. This results in more consistent cutter operation and consequently more predictable surgeries, while potentially extending the life of particular components, resulting in lower expenses to the patient.

Figure 1:
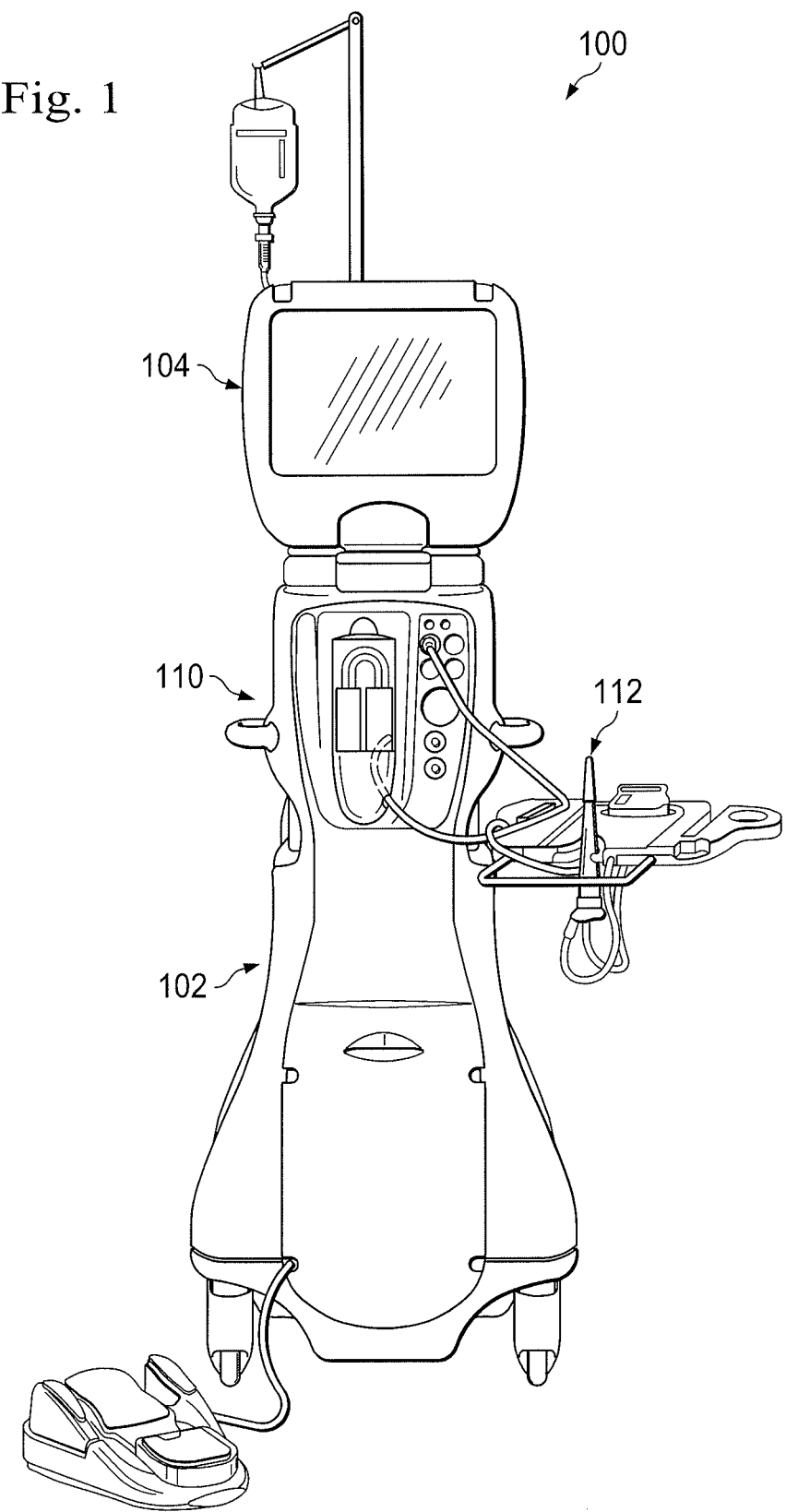
FIG. 1 is an illustration of an exemplary surgical machine according to one aspect of the present invention implementing the principles and methods described herein.

FIG. 1 illustrates a vitrectomy surgical machine, generally designated 100, according to an exemplary embodiment. The machine 100 includes a base housing 102 and an associated display screen 104 showing data relating to system operation and performance during a vitrectomy surgical procedure. The machine includes a vitrectomy cutter system 110 that includes a vitrectomy cutter 112 and is configured to provide feedback control to compensate for variations in operation due to mechanical inconsistencies created by tolerances, component wear, or other factors.

Figure 2:
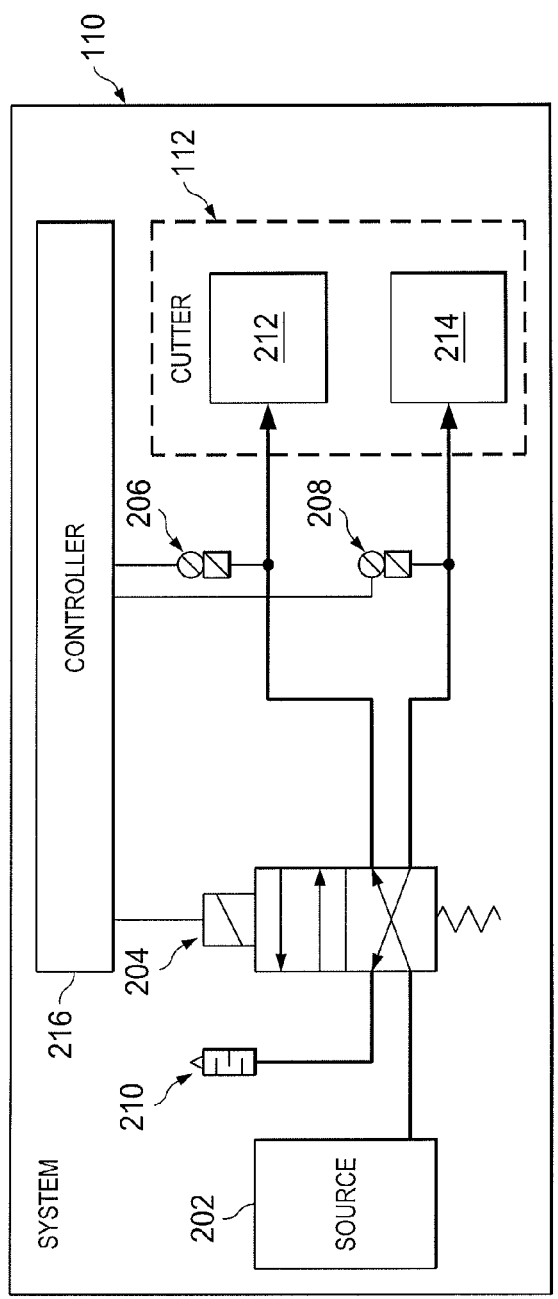
FIG. 2 is an diagram of an exemplary system on the surgical machine with feedback control according to one aspect of the invention.

FIG. 2 is a schematic of the vitrectomy cutter system 110 that provides feedback according to one exemplary embodiment. In FIG. 2, the cutter system 110 includes the vitrectomy cutter 112, a pneumatic pressure source 202, an adjustable directional on-off pneumatic actuator 204, pressure transducers 206, 208, a muffler 210, and a controller 216. As can be seen, the various components are in fluid communication with each other along lines representing flow paths or flow lines.

Figure 3:
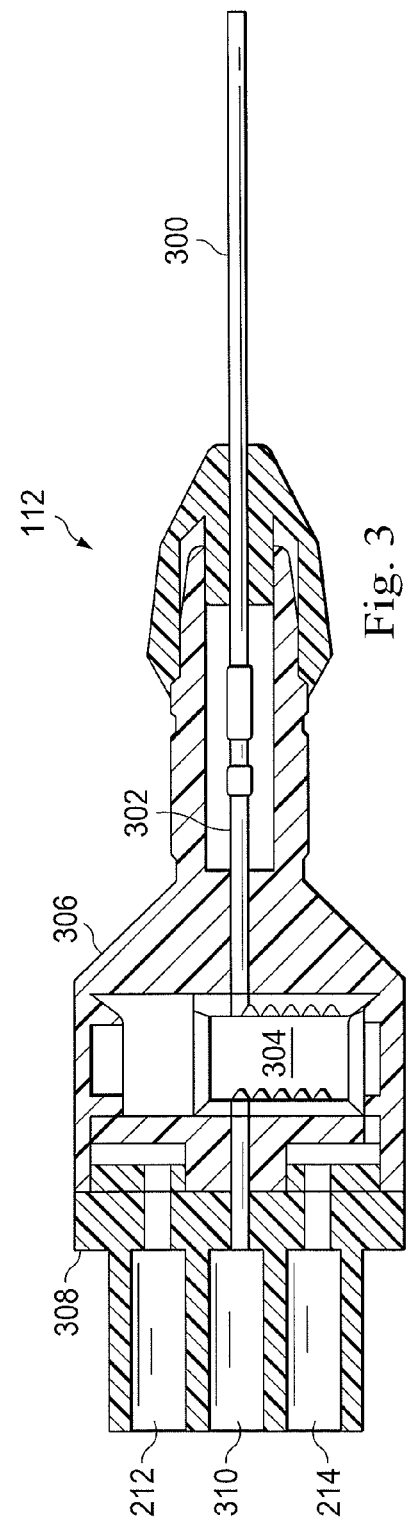
FIG. 3 is an illustration of an exemplary vitrectomy cutter in cross-section operable in accordance with the principles and methods described herein.

The vitrectomy cutter 112 is a pneumatically driven cutter having, as shown in FIG. 2, a first port 212 and a second port 214. It operates by receiving pneumatic pressure alternating through the first and second ports 212, 214. FIG. 3 shows a cross-sectional illustration of an exemplary vitrectomy cutter, referenced by the numeral 112. The cutter 112 includes as its basic components an outer cutting tube 300, an inner cutting tube 302, and a reciprocating air driven piston 304, all partially encased by a housing 306. The housing 306 includes an end piece 308 at the cutter proximal end with the first and second air supply ports 212, 214 (also in FIG. 2) and one suction port 310.

The exemplary cutter 112 operates by moving the inner cutting tube 302 past a tissue-receiving suction port (not shown) in the outer cutting tube 300. The inner cutting tube 302 and the outer cutting tube 300 cut tissue using a shearing action, similar to that of a scissors, as the inner tube reciprocates to open and close the tissue receiving port. A close fit between the tubes prevents vitreous material from being pulled into the space between the inner and outer cutting tubes when the inner cutting tube 302 opens the tissue-receiving suction port.

In one example of operation, if air pressure is increased at the first port 212, the piston 304 will move down, displacing the inner cutting tube 302 relative to the outer cutting tube 300, thereby closing the tissue-receiving suction port of the outer cutting tube 300. This cuts any vitreous material which may have been aspirated into the tissue-receiving suction port. Venting the pressure at the first port 212 and increasing the pressure at the second port 214 will move the piston up, opening the tissue-receiving suction port so that it can draw in new vitreous material to be cut. The operation of one exemplary cutter is described in greater detail in U.S. Pat. No. 5,176,628, incorporated herein by reference. Other exemplary cutters include flexible diaphragms in place of the piston for opening and closing the tissue-receiving port. However, any cutter having reciprocating action driven by alternating pneumatic pressure may be suitable for use with the system disclosed herein. In some examples, the vitrectomy cutter 112 is designed to provide about 5,000 cuts per minute, although both higher and lower cut rates are contemplated.

Returning to FIG. 2, in the example shown, the vitrectomy cutter system's on-off pneumatic actuator 204 is a standard four-way on-off valve. As is commonly known, the pneumatic actuator has a solenoid that operates to move the actuator to one of the two on-off positions depicted in the example of FIG. 2. Here, the pneumatic actuator 204 is in a position to provide pneumatic pressure to the first port 212, and to vent pneumatic pressure from the second port 214. In this position, pneumatic pressure can pass from the pressure source 202, through the on-off pneumatic actuator 204, and to the first port 212 where the pneumatic pressure provides pneumatic power to the vitrectomy cutter. At the same time, pneumatic pressure at the second port 214 can pass through the on-off pneumatic actuator 204 to the muffler 210 where it is exhausted to the atmosphere. In the other position, the on-off pneumatic actuator 204 allows pneumatic pressure to pass from the pressure source 202 to the second port 214 where the pneumatic pressure provides pneumatic power to the vitrectomy cutter 112. At the same time, pneumatic pressure at the first port 212 can vent through the on-off pneumatic actuator 204 to the muffler 210 where it is exhausted to the atmosphere. The on-off pneumatic actuator is configured to receive operating signals from the controller 216 as further described below.

In operation, pneumatic pressure is directed alternately from the source 202 to the first and second ports 212, 214 to operate the vitrectomy cutter 112. The on-off pneumatic actuator 204 alternates between its two positions very rapidly to alternatingly provide pneumatic pressure to the first and second ports 212, 214.

Although shown with a single pneumatic actuator 204, other embodiments include two pneumatic actuators, one associated with each of the two ports 212, 214. These embodiments operate similar to the manner described, with the actuators being are configured to independently receive operating signals from the controller 216.

The pressure transducers 206, 208 operate to detect pneumatic pressure levels at the respective first and second ports 212, 214. These pressure transducers 206, 208 may be standard pressure transducers capable of detecting compressed pneumatic pressure levels and communicating data representing the detected pressure levels to the controller 216.

In different embodiments, the controller 216 is, for example, a PID controller, an integrated circuit configured to perform logic functions, or a microprocessor that performs logic functions. It may include a memory and a processor that may execute programs stored in the memory. In some embodiments, the memory stores minimum threshold pressures, particular desired time lengths, and desired peak pressures, among other parameters, for particular duty cycles or cut rates of the vitrectomy cutter 112.

In some embodiments, the controller 216 is configured to provide a timing function that tracks the amount of time that measured pressures are above stored threshold pressures. The controller 216 is in communication with the on-off pneumatic actuator 204 and the pressure transducers 206, 208. As described below, the controller 216 is configured to control operation of the pneumatic actuator 204 based on feedback received from the pressure transducers 206, 208.

Figure 4:
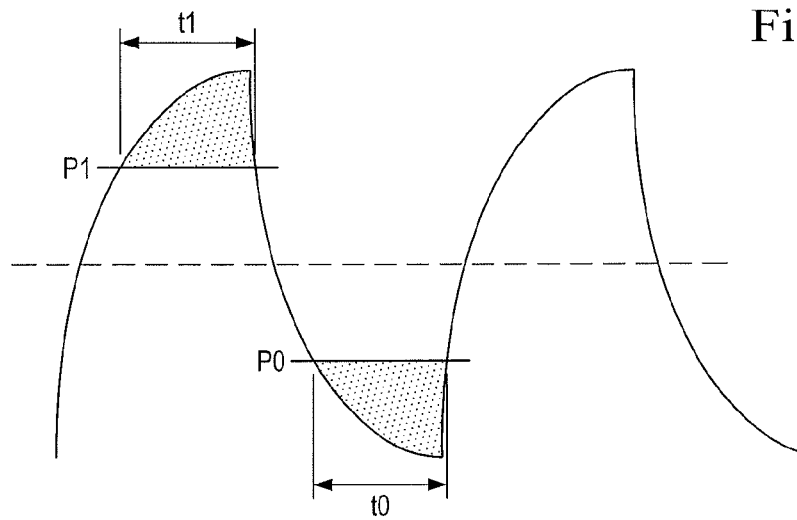
FIG. 4 is an illustration of an exemplary pressure wave form identifying a measured pressure characteristic and including thresholds and peaks in accordance with one aspect of the present invention.

FIG. 4 is an exemplary wave form 400 representing a pressure wave at a particular duty cycle. The pressure above the median represents pressure detected by the first pressure transducer 206 at the first port 212 and the pressure below the median represents the pressure detected by the second pressure transducer 208 at the second port 214.

The wave form 400 includes minimum pressure thresholds (P0, P1) that are input and stored in the controller 216. These minimum pressure thresholds (P0, P1) are threshold pressure values that must be met or exceeded in order to operate the vitrectomy cutter to fully open or close the tissue receiving port. For a vitrectomy cutter to operate at a desired cut rate or duty cycle, the actual pressures (p0, p1) at the pneumatic ports must 212, 214 exceed the minimum pressure thresholds (P0, P1) for a desired length of time (T0, T1) corresponding to the desired cut rate or duty cycle. This is described below with reference to the exemplary vitrectomy cutter 112 in FIG. 3.

In operation, the pressure transducer 206 measures the actual pressure (p1) at the first port 212. To actuate the pneumatic piston 314 in FIG. 3 in one direction to close the tissue-receiving port, the actual pressure (p1) must meet or exceed the minimum threshold pressure (P1) shown in FIG. 4. If the minimum threshold pressure (P1) is not met or exceeded, the pneumatic piston 304 may not displace far enough to fully close the tissue receiving port in the outer cutting tube 300 in the cutter in FIG. 3. In addition, by controlling the length of time that the actual pressure (p1) is at or exceeding the minimum threshold pressure (P1), the system controls the duty cycle. As the time at or exceeding the threshold pressure (P1) changes, so does the cut rate or duty cycle.

Similarly, the pressure transducer 208 measures the actual pressure (p0) at the second port 214. To actuate the pneumatic piston 304 in FIG. 3 in the opposite direction to open the tissue-receiving port, the actual pressure (p0) must meet or exceed the minimum threshold pressure (P0). Consequently, failure to meet the minimum threshold pressure (P0) may result in only a partially open tissue receiving port in the cutter in FIG. 3. Further, as above, the actual pressure (p0) should meet or exceed the minimum threshold pressure (P0) for a desired length of time (T0) corresponding to the desired cut rate or duty cycle.

In conventional systems, variations in actuator characteristics due to initial tolerances or degradation and wear over time could potentially degrade the performance of the actuator or even prevent the actuator from fully opening or fully closing.

However, in the present system, the controller 216 is configured to compensate for component tolerances and variations by measuring and tracking the actual time (t0, t1) that the measured actual pressures (p0, p1) are above the respective minimum pressure thresholds (P0, P1). By comparing the actual time (t0, t1) to the desired time (T0, T1), the controller 216 may calculate a difference or margin usable to modify the control signals sent to the on-off pneumatic actuator 204 to adjust the cutter's duty cycle. In can do this based on control laws that determine whether adjustments should be made to signals being sent to the on-off pneumatic actuator 204. This becomes more clear with reference to an exemplary method below of generating and using feedback control for the pneumatic on-off pneumatic actuator 204.

Figure 5:
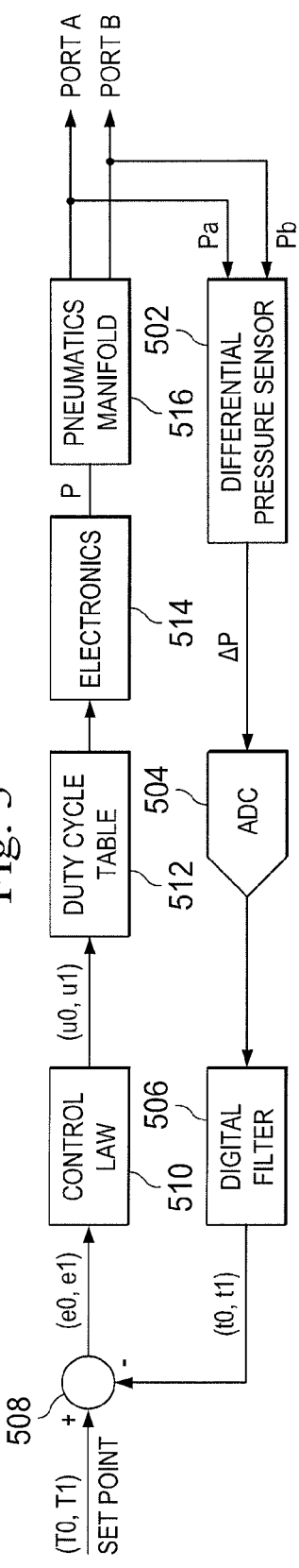
FIG. 5 is an illustration of an exemplary model showing feedback control steps in accordance with one aspect of the present invention.

FIG. 5 shows an exemplary control loop 500 for generating and using feedback control to reduce errors due to component variation, such as may occur with, for example, tolerance build up or wear. An exemplary method of feedback control will be described with reference to the control loop 500.

In use, the system 110 receives an input from a health care provider setting a particular cut rate and/or duty cycle. This may be done using an input device on the machine 100, may be input by controlling an input on the vitrectomy cutter 112. Input examples may include squeezing the cutter handle to adjust the duty cycle, inputting via selection on a screen using a keyboard, mouse, knobs, or other known input device. In some examples, the setting is prestored in the system using default or pre-programmed values. The system then initializes and operates at that particular setting and controls the on-off pneumatic actuator 204 to pneumatically actuate the cutter 112. Based on the inputs or pre-stored data, the controller 216 stores data representing minimum pressure thresholds (P0, P1) that must be met or exceeded at each port to fully open and close the tissue receiving port on the vitrectomy cutter.

The feedback control begins at the differential pressure sensor 502. With reference to the example described above, the differential pressure sensor 502 represents the first and second pressure transducers 206, 208. However, in other embodiments, other pressure sensor arrangements are used, including in some embodiments, only a single pressure sensor. Returning to the example disclosed herein, the feedback control begins when the differential pressure sensor 502 detects the actual pneumatic pressures (p0, p1) at the first and second ports 212, 214. The differential pressure sensor 502 may be physically associated with pneumatic flow lines on the machine 100, may be on the cutter 112 itself, or elsewhere located, so long as it is able to detect the pressure representative of or indicative of pressure at the first and second ports 212, 214.

The differential pressure sensor 502 outputs data indicative of the actual pressures (p0, p1) in the first and second ports 212, 214 as an analog signal. In this example, an analog to digital converter (ADC) 504 converts the analog signal to digital form. Although shown as a separate element in FIG. 5, the ADC 504 may be physically associated with the differential pressure sensor 502, may be a part of the controller 216, or may be disposed in between.

In some embodiments, the ADC 504 is also configured in a manner that tracks the actual length of time (t0, t1) that the measured pressures (p0, p1) meet or exceed pre-stored minimum pressure thresholds (P0, P1). These minimum pressure thresholds (P0, P1) represent pressures required to fully open or fully close the tissue-receiving port on the cutter. Therefore, the actual length of time (t0, t1) is indicative of the actual length of time that the tissue receiving port is fully open or fully closed. The actual length of time (t0, t1) may be for a single cutting cycle, or may be averaged over a plurality of cutting cycles. The ADC 504 then outputs the actual length of time (t0, t1). In some embodiments, the controller 216 tracks the time instead of the ADC 504.

In FIG. 5, the digital signal is then filtered by a digital filter 506 in a manner known in the art to provide meaningful data for treatment by a summing module 508 executable in the controller 216. The summing module 508 is configured to detect an error or margin (e0, e1) in lengths of time for both the time the tissue-receiving port is fully open and the time the tissue-receiving port is fully closed. This is based on the actual length of time (t0, t1) compared to the desired length of time (T0, T1) for the selected cutting rate and/or duty cycle. These may be averaged over a number of cycles. One exemplary process for determining the margins (e0, e1) is set forth below.

In one example, the summing module determines the margins (e0, e1) using simple summing calculations. An example of these is provided below:

$$e0 = t0 - T0 = \text{(actual length of time)} - \text{(desired length of time)}; \text{ and}$$

$$e1 = t1 - T1 = \text{(actual length of time)} - \text{(desired length of time)}.$$

The margin e0 represents the margin in one actuator position. For example, the actuator position may be a position that provides pneumatic pressure to open the tissue-receiving port on the vitrectomy cutter 112. The margin e1 represents the margin in the opposing actuator position. For example, the opposing actuator position may be a position that provides pneumatic pressure to close the tissue-receiving port on the vitrectomy cutter 112. In some embodiments, the margins are based on averages taken over a plurality of cycles.

In some embodiments, the summing module 508 calculates E, representing the asymmetry between the two margins at the two positions. The may be done using the below equation.

$$E = e1 - e0.$$

Figure 6:
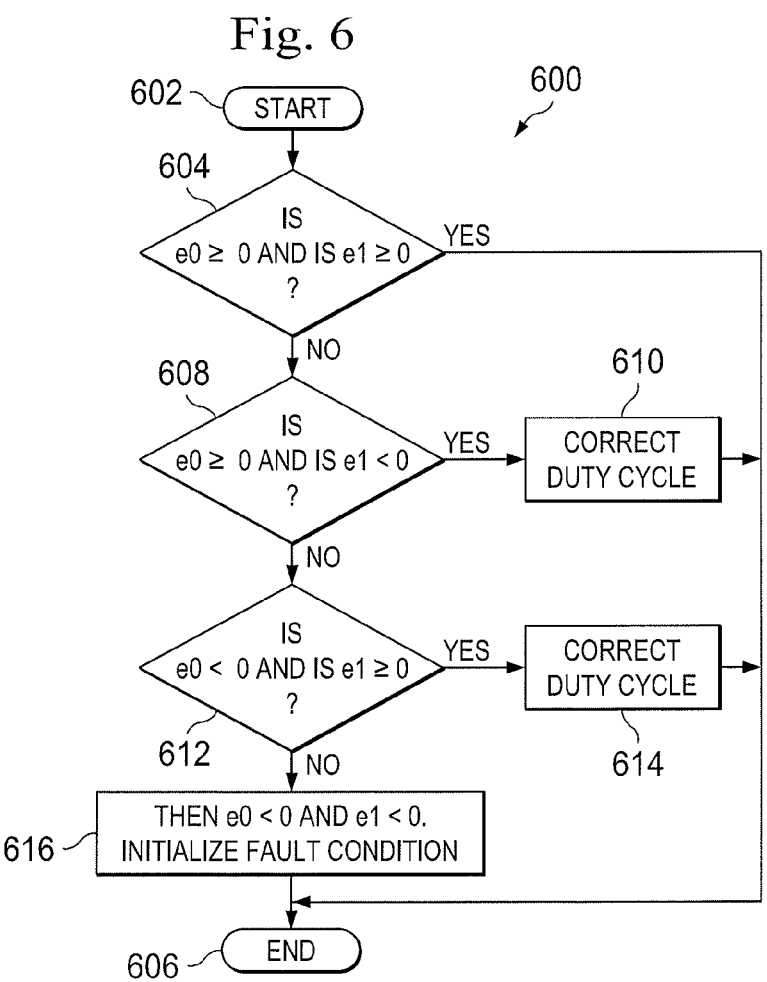
FIG. 6 is an illustration of a flow chart showing exemplary steps for determining adjustments to stored operating parameters in accordance with one aspect of the present invention.

Based upon the calculated margins (e0, e1), the controller 216 uses control laws 510 to determine whether changes should be made to the duty cycle data used to control the pneumatic actuator 204. One exemplary control law, referenced herein by the numeral 600, is explained with reference to FIG. 6. The control law 600 in FIG. 6 starts at a step 602.

At step 604, the control law queries whether the margin e0 and the margin e1 are both equal to or greater than zero. If yes, then the system is operating correctly because the actual length of time (t0, t1) that the actual pressure (p0, p1) is at or above the minimum pressure threshold (P0, P1) is equal to or greater than the desired length of time (T0, T1). Accordingly, the duty cycle and cut rate need not change and the query ends at step 606. Alternatively, in some embodiments, if necessary, the system may still use the asymmetry E as the loop error to increase or decrease the duty cycle using the controller 216 to provide more exact operation.

If the answer is no at step 604, the control law queries whether e0 is greater than or equal to zero and e1 is less than zero at step 608. If yes, then the system corrects the duty cycle at step 610 using E as the loop error to increase the amount of time that pneumatic pressure is directed to port 214 by controlling the pneumatic actuator 204. Correcting the duty cycle may include adjusting or updating stored operating data used to generate timing signals for a particular duty cycle. The control law then ends at step 606.

If the answer is no at step 608, then the system queries whether e0 is less than zero and e1 is equal to or greater than zero at a step 612. If yes, then the system corrects the duty cycle at step 614 using E as the loop error to increase the amount of time that pneumatic pressure is directed to port 212 by controlling the pneumatic actuator 204. The control law then ends at step 606.

Steps 608 and 610 determine whether the amount of time the actuator is opened should be increased or should be decreased. In some embodiments, the asymmetry E represents the amount of the increase or decrease. In other embodiments, the calculated margins (e0, e1) represent the amount of the increase or decrease.

If the answer is no at step 612, then both e0 and e1 are less than zero, as indicated at step 616. Therefore, the system enters a fault condition because a duty cycle correction is insufficient to correct the condition. A potential cause of such a condition at step 616 is a low source pressure, resulting in an amplitude insufficient to meet the minimum threshold pressures to fully open or to fully close the tissue receiving port in the cutter 112. Another potential cause of such a condition is that the cut rate is higher than can be sustained by the system at the current operating parameters.

When a fault condition is entered, the system may notify the health care provider with an audible, visual, or tactile signal that the system is not in operating condition. In one exemplary embodiment, prior to initiating the fault condition, the system 110 may make efforts to control the pneumatic pressure source 202 to increase the source pressure. In this embodiment, if the source pressure is increased sufficiently, then the system may return to the start of the control law. If increasing the source pressure is not possible, then the fault condition may be triggered.

In another exemplary embodiment, if the pressure is unable to be sufficiently increased, the system may prompt the user with an indication that the cut rate may need to be decreased to achieve the desired duty cycle. Any change to cut rate may be done either manually at the user's instruction or automatically. The control law ends at step 606.

Returning to FIG. 5, after using the control law 510 to determine whether the duty cycle needs correction, if necessary, the system outputs the correction as (u0, u1). This correction (u0, u1) is then used to update the stored duty cycle control data 512 to more closely align the desired length of time (T0, T1) with the actual length of time (t0, t1) that the actual pressure (p0, p1) is above the minimum threshold pressure (P0, P1). In some examples, this is done by updating a table stored in the controller memory that tracks and associates the desired times with the desired cutting rates or duty cycles.

Using the updated duty cycle data, the system generates a control signal for controlling the pneumatic actuator 204. Here, since the pneumatic actuator may vary by type and number used, the pneumatic actuator is represented by the pneumatics manifold 516. The method may then repeat to continuously detect and correct deviations from desired values that may occur.

Figure 7:
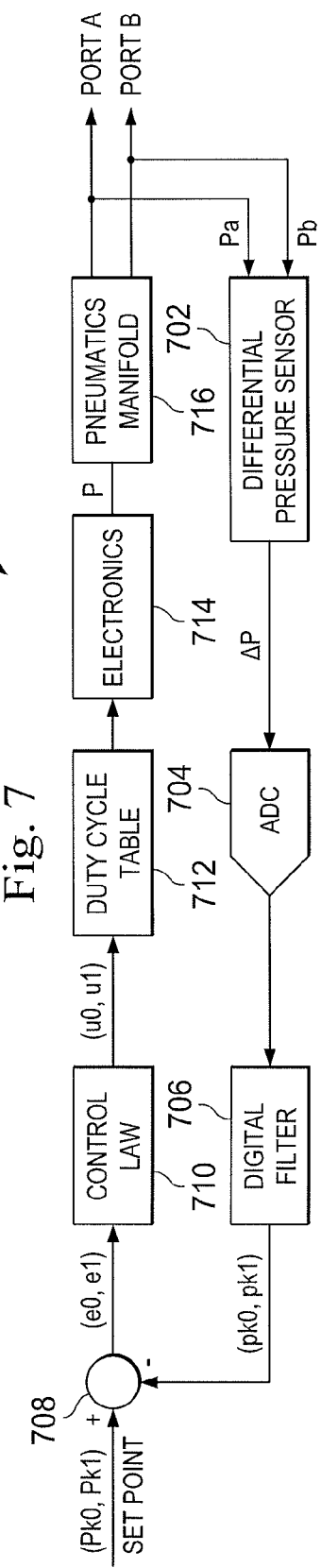
FIG. 7 is an illustration of an exemplary model showing the feedback control steps in accordance with another aspect of the present invention.

In another embodiment, the system 110 provides feedback based only upon detected pressure without monitoring the actual time spent above the minimum pressure thresholds. FIG. 7 shows an example of operation of this alternative control loop. In many respects, the alternative embodiment in FIG. 7 is similar to that described above in FIG. 5. Only differences are described in detail.

The control loop 700 operates in manner similar to that described above, where the system receives an input from a health care provider setting a particular cut rate and/or duty cycle. Based on the inputs or on pre-stored data, the controller 216 stores data representing peak pressures (PK0, PK1) that must be met at each port to fully open and close the tissue receiving port on the vitrectomy cutter for the length of time corresponding to the desired duty cycle or cut rate. The peak pressures represent the maximum pressures shown at the tips of the wave forms.

Here, the feedback control begins at the differential pressure sensor 702. The differential pressure sensor 702 outputs data indicative of the actual pressures (pk0, pk1) in the first and second ports 212, 214 as an analog signal. An ADC 704 converts the analog signal to digital form. In this embodiment, the ADC identifies the actual detected peak pressures (pk0, pk1). These are the maximum pressures identified by the pressure transducers 206, 208 for their respective port 212, 214.

The digital signal is then filtered by a digital filter 706 in a manner known in the art to provide meaningful data for treatment by a summing module 708 executable in the controller 216. The summing module 708 is configured to detect an error or margin (e0, e1) between desired peak pressures (PK0, PK1) and actual peak pressures (pk0, pk1). In this example, the summing module determines the margins (e0, e1) using simple summing calculations. These are provided below:

$$e0 = pk0 - PK0 = \text{(actual peak pressure)} - \text{(desired peak pressure)}; \text{ and}$$

$$e1 = pk1 - PK1 = \text{(actual peak pressure)} - \text{(desired peak pressure)}.$$

Again, the margins e0, e1 each represent the margin in different actuator positions. These actuator positions may be those that provide pneumatic pressure to fully open or fully close the tissue-receiving port on the vitrectomy cutter 112. The summing module 708 the calculates E, the asymmetry between the two margins at the two positions using the same equation described above.

$$E = e1 - e0.$$

Based upon the calculated margins (e0, e1), the controller 216 uses control laws 710 to determine whether changes should be made to the duty cycle data used to control the pneumatic actuator 204. In this embodiment, the control law is the same as the control law described with reference to FIG. 6.

After using the control law 710 to determine whether the duty cycle needs correction, if necessary, the system outputs the correction as (u0, u1). This correction (u0, u1) is then used to update the duty cycle 712 to more closely align the desired peak pressure (PK0, PK1) with the actual pressure (pk0, pk1).

Using the updated duty cycle data, the system generates a control signal for controlling the pneumatics manifold 716 with the on-off pneumatic actuator 204. The method may then repeat to continuously detect and correct deviations from desired values that may occur.

This feedback control can be used to reduce the overall sensitivity of the system to individual component tolerances, variations, and overall deviations from desired characteristics. This approach does not require factory calibration, can accommodate a wider range of critical component tolerances, and continues to compensate for changes as a result of component aging, or adverse environmental effects, such as temperature.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A surgical system having feedback control for pneumatic actuators, comprising:
   a pneumatic pressure source;
   a vitrectomy cutter having a cutting mechanism, a first pneumatic input port, and a second pneumatic input port;
   a pneumatic actuator configured to alternate pneumatic pressure to the first and second pneumatic input ports based on an actuator actuation timing;
   a first pressure transducer placed and configured to measure actual pressure at the first pneumatic input port;
   a second pressure transducer placed and configured to measure actual pressure at the second pneumatic input port; and
   a controller in communication with the first and second pressure transducers and the pneumatic actuator, the controller being configured to measure an actual length of time the measured actual pressure of the first pressure transducer is above a minimum pressure threshold and further configured to change the pneumatic actuator actuation timing based on comparing the actual length of time the measured actual pressure of the first pressure transducer is above the minimum pressure threshold to a desired length of time that the measured actual pressure is desired to be above the minimum pressure threshold.

2. The surgical system of claim 1, wherein the controller is configured to measure an actual length of time the measured actual pressure of the second pressure transducer is above a minimum pressure threshold and further configured to change the pneumatic actuator actuation timing based on comparisons of the actual length of times the measured actual pressure for the first pressure transducer and the measured actual pressure for the second pressure transducer are above the minimum pressure threshold to desired length of times that the measured actual pressures for the first pressure transducer and the second pressure transducer are desired to be above the minimum pressure threshold.

3. The surgical system of claim 2, wherein the minimum pressure threshold corresponds to a pressure required to actuate the cutting mechanism on the vitrectomy cutter.

4. The surgical system of claim 2, wherein the controller is configured to compare the actual length of times to a desired length of time corresponding to a desired duty cycle.

5. The surgical system of claim 1, wherein the controller is configured to increase the amount of time the pneumatic actuator directs pneumatic pressure to the first input port when the actual length of time is shorter than the desired length of time.

6. The surgical system of claim 1, wherein the controller is configured to decrease the amount of time the pneumatic actuator directs pneumatic pressure to the first input port when the actual length of time is longer than the desired length of time.

7. The surgical system of claim 2, wherein the controller is configured to determine an amount of time that the measured actual pressure at the first and second input ports is above a minimum pressure threshold by averaging the measured actual length of times over a plurality of cycles.

8. The surgical system of claim 1, wherein the controller is configured to modify the actuation timing by adjusting settings for the actuator stored in a memory.

9. The surgical system of claim 1, wherein the controller is configured to activate a fault condition when the actual pressures at the first and second pneumatic input ports are below fault threshold pressure levels.

10. The surgical system of claim 1, wherein the controller is configured to use the actual length of time as feedback control to detect and compensate for deviations in operation, through adjustment of the pneumatic actuator actuation timing, due to inconsistencies arising from tolerances or degradation of the pneumatic actuator.

11. A method of controlling a surgical system using feedback control for pneumatic actuators, comprising:
  alternating pneumatic pressure to first and second pneumatic input ports on a vitrectomy cutter based on an actuation timing;
  measuring actual pressure at the first pneumatic input port with a first pressure transducer;
  measuring actual pressure at the second pneumatic input port with a second pressure transducer; and
  measuring an actual length of time the measured actual pressure of the first pressure transducer is above a minimum pressure threshold;
  comparing the actual length of time the measured actual pressure of the first pressure transducer is above the minimum pressure threshold to a desired length of time that the measured actual pressure is desired to be above the minimum pressure threshold; and
  modifying the actuation timing of the pneumatic actuator based on the comparison to move the actual length of time closer to the desired length of time.

12. The method of claim 11, comprising:
  measuring an actual length of time that the measured actual pressure at the second pneumatic input port is above the minimum pressure threshold;
  comparing the actual length of times the measured actual pressure for the first pressure transducer and the measured actual pressure for the second pressure transducer are above the minimum pressure threshold to desired length of times that the measured actual pressures for the first pressure transducer and the second pressure transducer are desired to be above the minimum pressure threshold; and
  modifying the actuation timing of the pneumatic actuator based on the comparison to move the actual length of times closer to the desired length of times.

13. The method of claim 12, comprising comparing the measured actual lengths of time to the desired lengths of time corresponding to a desired cut rate or duty cycle to determine a margin.

14. The method of claim 13, comprising:
  evaluating the margin using a control law; and
  updating a duty cycle table to improve operational accuracy based on the determined margin.

15. The method of claim 11, wherein measuring pneumatic pressure and modifying actuation timing occur during a surgical procedure.

16. The method of claim 11, further comprising:
  storing a desired peak pressure; and
  comparing the measured actual pressure to the desired peak pressure to determine an error or margin.

17. The method of claim 12, wherein modifying actuation timing of the pneumatic actuator comprises:
  increasing the amount of time the pneumatic actuator directs pneumatic pressure to the first input port when the measured actual length of time that the measured actual pressure of the first pressure transducer is above a minimum pressure threshold is shorter than a desired length of time; and
  decreasing the amount of time the pneumatic actuator directs pneumatic pressure to the first input port when the measured actual length of time that the measured actual pressure of the first pressure transducer is above a minimum pressure threshold is longer than the desired length of time.

18. The method of claim 12, further comprising determining an amount of time that the measured actual pressure at the first and second input ports is above a minimum pressure threshold by averaging the measured actual length of times over a plurality of cycles.

19. The method of claim 11, wherein comparing the actual length of time to the desired length of time implements feedback control to detect and compensate for deviations in operation, through modifying the actuation timing of the pneumatic actuator, due to inconsistencies arising from tolerances or degradation of the pneumatic actuator.

* * * * *